US 8,357,958 B2

(12) United States Patent
Cummins

(10) Patent No.: US 8,357,958 B2
(45) Date of Patent: Jan. 22, 2013

(54) INTEGRATED CMOS POROUS SENSOR

(75) Inventor: Timothy Cummins, County Clare (IE)

(73) Assignee: Silicon Laboratories Inc., Austin, TX (US)

( * ) Notice: Subject to any disclaimer, the term of this patent is extended or adjusted under 35 U.S.C. 154(b) by 53 days.

(21) Appl. No.: 13/065,293

(22) Filed: Mar. 18, 2011

(65) Prior Publication Data

US 2011/0226041 A1    Sep. 22, 2011

Related U.S. Application Data

(60) Continuation-in-part of application No. 12/453,965, filed on May 28, 2009, which is a division of application No. 11/092,725, filed on Mar. 30, 2005, now Pat. No. 7,554,134, application No. 13/065,293, which is a continuation of application No. 11/992,470, filed as application No. PCT/IE2006/000107 on Oct. 2, 2006, now Pat. No. 8,007,167.

(60) Provisional application No. 60/558,565, filed on Apr. 2, 2004, provisional application No. 60/721,968, filed on Sep. 30, 2005.

(51) Int. Cl.
*H01L 29/66* (2006.01)
*H01L 29/80* (2006.01)
*G01N 27/02* (2006.01)
*G01N 27/12* (2006.01)
*G01N 27/22* (2006.01)

(52) U.S. Cl. .................. 257/253; 73/335.03; 73/335.04

(58) Field of Classification Search ............... 73/335.03, 73/335.04, 335.05, 31.06; 257/252, 253
See application file for complete search history.

(56) References Cited

U.S. PATENT DOCUMENTS 4,057,823 A    11/1977    Burkhardt et al.
(Continued)

FOREIGN PATENT DOCUMENTS

JP    358111747    7/1983
(Continued)

OTHER PUBLICATIONS

K. Banerjee, S. J. Souri, P. Kapur, and K. C. Saraswat, "3-D ICs: A novel ship design for improving deep-submicrometer interconnect performance and systems-on-chip integration," Proceedings of IEEE, vol. 89, No. 5, May 2001, pp. 602-633.*

(Continued)

*Primary Examiner* — Lisa Caputo
*Assistant Examiner* — Punam Roy
(74) *Attorney, Agent, or Firm* — O'Keefe, Egan, Peterman & Enders LLP

(57) ABSTRACT

A single chip wireless sensor comprises a microcontroller connected to a transmit/receive interface, which is coupled to a wireless antenna by an L-C matching circuit. The sensor senses gas or humidity and temperature. The device is an integrated chip manufactured in a single process in which both the electronics and sensor components are manufactured using standard CMOS processing techniques, applied to achieve both electronic and sensing components in an integrated process. A Low-K material with an organic polymer component is spun onto the wafer to form a top layer incorporating also sensing electrodes. This material is cured at 300° C., which is much lower than CVD temperatures. The polyimide when cured becomes thermoset, and the lower mass-to-volume ratio resulting in K, its dielectric constant, reducing to 2.9. The thermoset dielectric, while not regarded as porous in the conventional sense, has sufficient free space volume to admit enough gas or humidity for sensing.

14 Claims, 13 Drawing Sheets

U.S. PATENT DOCUMENTS

| | | | |
|---|---|---|---|
| 4,542,640 A * | 9/1985 | Clifford | 73/31.06 |
| 4,580,439 A | 4/1986 | Manaka | |
| 4,638,346 A | 1/1987 | Inami et al. | |
| 4,649,364 A | 3/1987 | Tanahashi et al. | |
| 4,793,181 A | 12/1988 | Djorup | |
| 4,831,381 A | 5/1989 | Hester | |
| 4,849,798 A | 7/1989 | Wantanabe | |
| 4,876,890 A | 10/1989 | Mercer et al. | |
| 4,931,851 A | 6/1990 | Sibbald et al. | |
| 5,296,125 A | 3/1994 | Glass et al. | |
| 5,357,149 A | 10/1994 | Kimura | |
| 5,481,129 A | 1/1996 | DeJong et al. | |
| 5,801,428 A | 9/1998 | Felde et al. | |
| 5,878,332 A | 3/1999 | Wang et al. | |
| 6,017,775 A | 1/2000 | Igel et al. | |
| 6,051,854 A | 4/2000 | Vigna et al. | |
| 6,111,280 A | 8/2000 | Gardner et al. | |
| 6,407,449 B1 | 6/2002 | Takikawa et al. | |
| 6,417,026 B2 | 7/2002 | Gotoh et al. | |
| 6,484,559 B2 * | 11/2002 | Dodabalapur et al. | 73/23.34 |
| 6,647,782 B2 | 11/2003 | Toyoda | |
| 6,673,644 B2 | 1/2004 | Gole et al. | |
| 6,690,569 B1 | 2/2004 | Mayer et al. | |
| 6,724,612 B2 | 4/2004 | Davis et al. | |
| 6,774,613 B1 | 8/2004 | Becker et al. | |
| 7,554,134 B2 | 6/2009 | Cummins | |
| 7,622,080 B2 | 11/2009 | Enquist | |
| 7,709,828 B2 | 5/2010 | Braithwaite et al. | |
| RE41,889 E | 10/2010 | Ferrari et al. | |
| 7,888,708 B2 | 2/2011 | Yazawa et al. | |
| 2002/0141136 A1 | 10/2002 | Toyoda et al. | |
| 2003/0010119 A1 | 1/2003 | Toyoda | |
| 2003/0010988 A1 | 1/2003 | Franson | |
| 2004/0008471 A1 | 1/2004 | Davis et al. | |
| 2005/0097941 A1 | 5/2005 | Sandvik et al. | |
| 2005/0188764 A1 | 9/2005 | Itakura et al. | |
| 2005/0199975 A1 | 9/2005 | Matubara | |
| 2006/0090541 A1 * | 5/2006 | Theil | 73/23.34 |
| 2008/0061323 A1 | 3/2008 | Yazawa et al. | |
| 2009/0141767 A1 | 6/2009 | Cummins | |
| 2009/0273009 A1 | 11/2009 | Cummins | |

FOREIGN PATENT DOCUMENTS

| | | |
|---|---|---|
| JP | 63103957 | 10/1986 |
| JP | 404361149 | 12/1992 |

OTHER PUBLICATIONS

Cummins, "Integrated CMOS Porous Sensor", U.S. Appl. No. 12/453,965, Response to Office Action, Jul. 20, 2011, 9 pgs.
International Search Report, PCT/IE2005/000033, 2005, 5 pgs.
Cummins, "An Integrated CMOS Porous Sensor", U.S. Appl. No. 11/092,725, Notice of Allowance and Fees Due, Feb. 27, 2009, 6 pgs.
Cummins, "An Integrated CMOS Porous Sensor", U.S. Appl. No. 11/092,725, Interview Summary, Feb. 2, 2009, 2 pgs.
Cummins, "An Integrated CMOS Porous Sensor", U.S. Appl. No. 11/092,725, Amendment After Final Rejection, Jan. 28, 2009, 15 pgs.
Cummins, "An Integrated CMOS Porous Sensor", U.S. Appl. No. 11/092,725, Final Office Action, Oct. 28, 2008, 12 pgs.
Cummins, "An Integrated CMOS Porous Sensor", U.S. Appl. No. 11/092,725, Amendment Under 37 CFR 1.111, Mar. 31, 2008, 15 pgs.
Cummins, "An Integrated CMOS Porous Sensor", U.S. Appl. No. 11/092,725, Office Action, Nov. 30, 2007, 13 pgs.
Cummins, "Integrated MOS Wireless Sensor", U.S. Appl. No. 12/977,358, Application, Dec. 23, 2010, 30 pgs.
Cummins, "An Integrated CMOS Porous Sensor", U.S. Appl. No. 12/975,846, Application, Dec. 22, 2010, 30 pgs.
Lemme, Elektronik, "CMOS-Sensoren gehort die Zukunft", vol. 43, No. 24, Nov. 1994, 10 pgs.
Bousse et al., "A Process for the Combined Fabrication of Ion Sensors and CMOS Circuits", IEEE Electron Device Letters, vol. 9, No. 1, Jan. 1988, 3 pgs.
Baltes et al., "Micromachined Thermally Based CMOS Microsensors", Proceedings of The IEEE, vol. 86, No. 8, Aug. 1998, 19 pgs.
Baltes et al., "The Electronic Nose in Lilliput", Proceedings of the IEEE, vol. 35, No. 9, Sep. 1998, 4 pgs.
International Search Report, PCT/06/000107, Jan. 22, 2007, 3 pgs.
McCartney et al., "A Fully Integrated Sensor Interface Chip", Solid State Circuits Conference Esscirc, 1999, 4 pgs.
Cratlon, "C701 802.15.4 Zigbee Ready Wireless Sensor Module", 2004, 1 pg.
Cummins, "Integrated Electronic Sensor", U.S. Appl. No. 11/992,470, Office Action, Sep. 22. 2010, 6 pgs.
Cummins, "Integrated Electronic Sensor", U.S. Appl. No. 11/992,470, Response to Restriction Requirement, Oct. 14, 2010, 2 pgs.
Cummins, "Integrated Electronic Sensor", U.S. Appl. No. 11/992,470, Office Action, Jan. 4, 2011, 14 pgs.
Cummins, "Integrated Electronic Sensor", U.S. Appl. No. 11/992,470, Response to Office Action, Feb. 25, 2011, 11 pgs.
Cummins, "Integrated MOS Sensor Having Temperature Sensor", U.S. Appl. No. 12/977,370, Application, Dec. 23, 2010, 30 pgs.
Cummins, "Integrated CMOS Porous Sensor", U.S. Appl. No. 12/453,965, Office Action, Oct. 18, 2011, 13 pgs.
Cummins, "Integrated CMOS Porous Sensor", U.S. Appl. No. 12/453,965, Response to Office Action, Nov. 30, 2011, 9 pgs.
Cummins, "Integrated Electronic Sensor", U.S. Appl. No. 11/992,470, Notice of Allowance and Issue Fee Due, May 9, 2011, 7 pgs.
Cummins, "Integrated CMOS Porous Sensor", U.S. Appl. No. 12/453,965, Office Action, Jun. 27, 2011, 22 pgs.
Cummins, "An Integrated CMOS Porous Sensor", U.S. Appl. No. 13/494,392, Application, Jun. 12, 2012, 32 pgs.

* cited by examiner

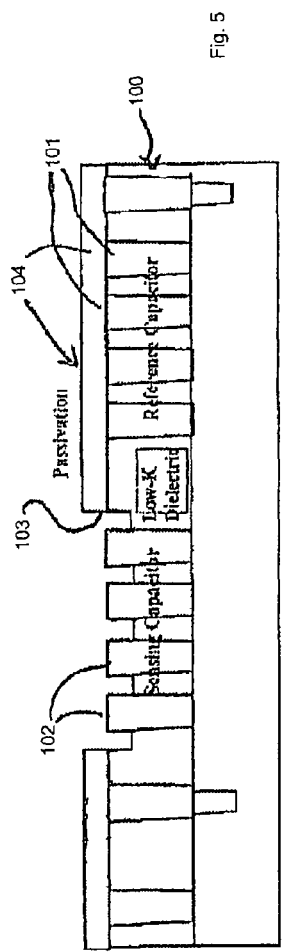
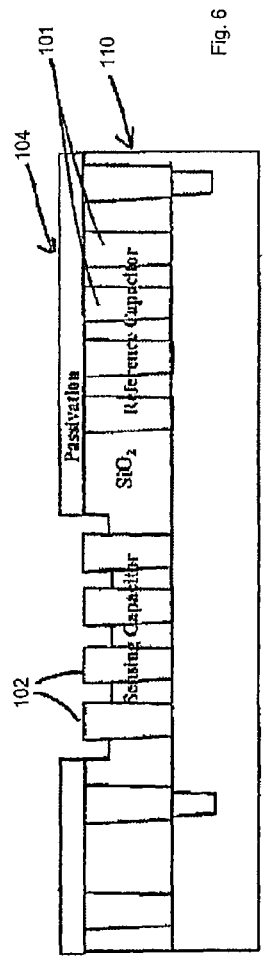
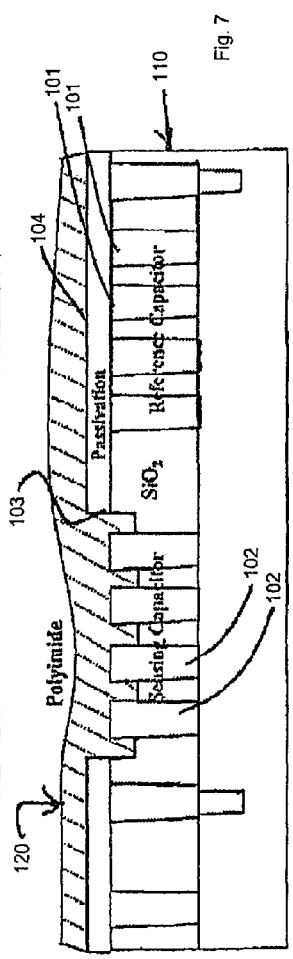
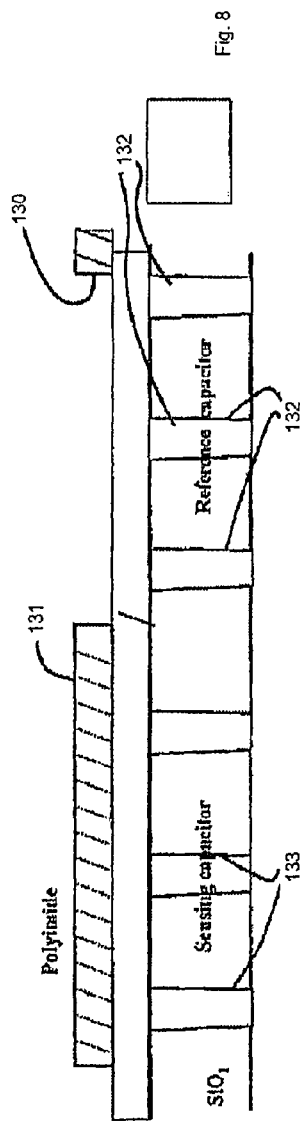

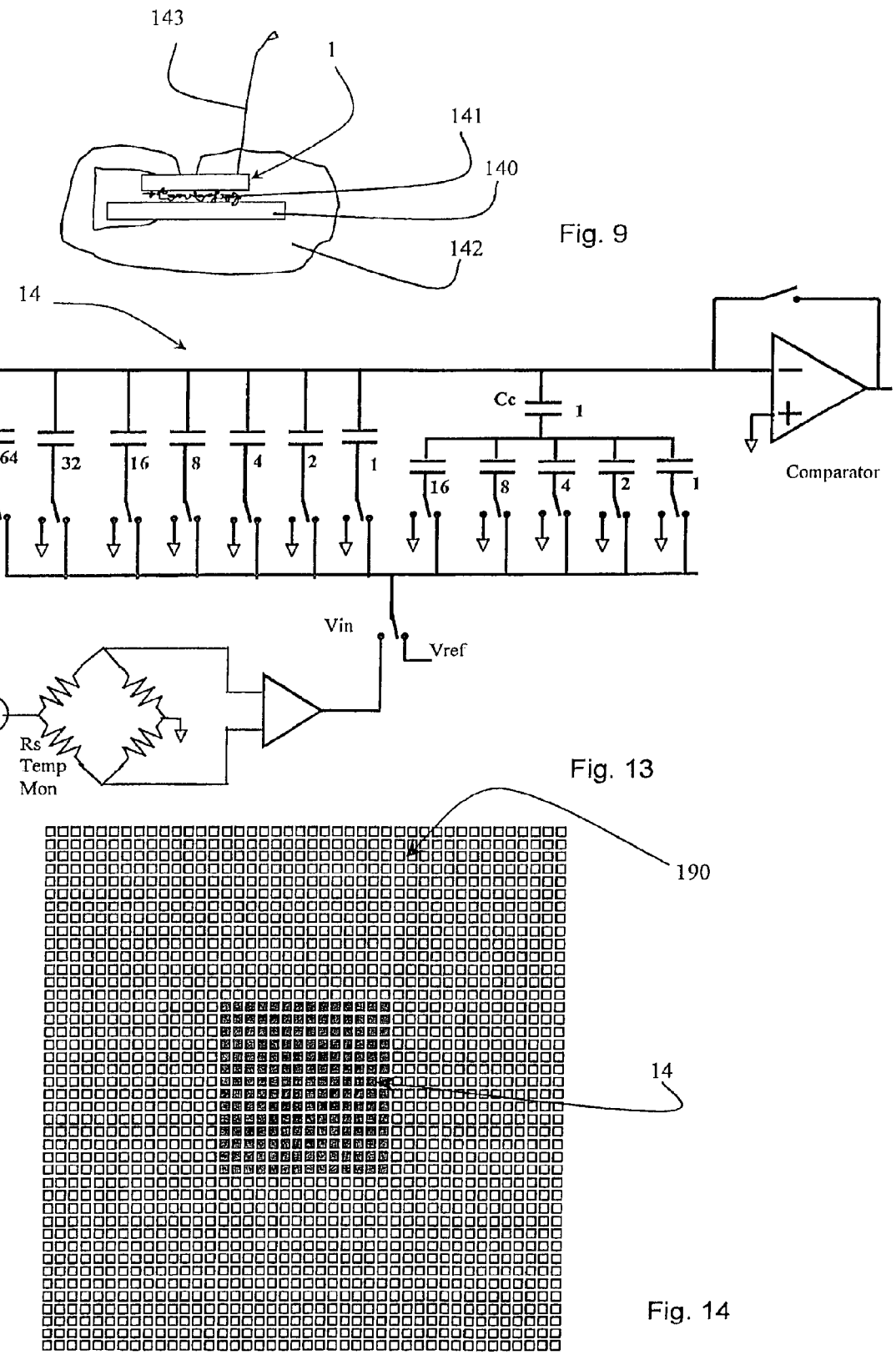

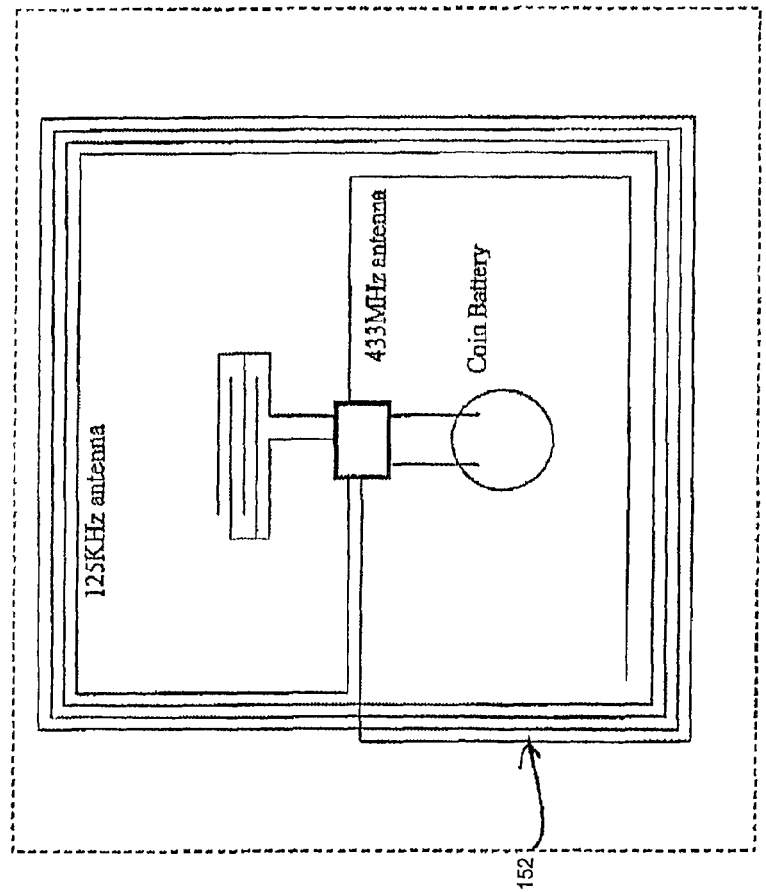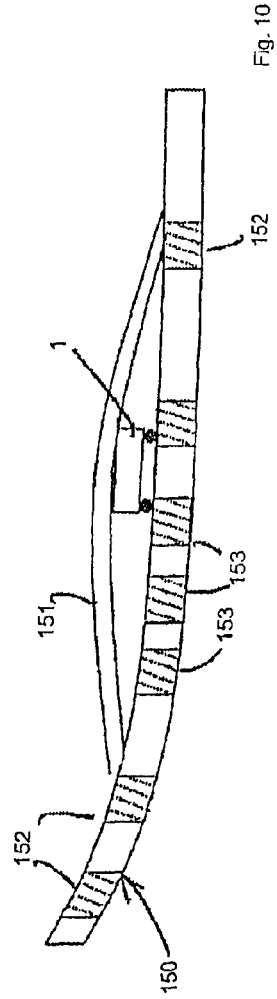
Fig. 10

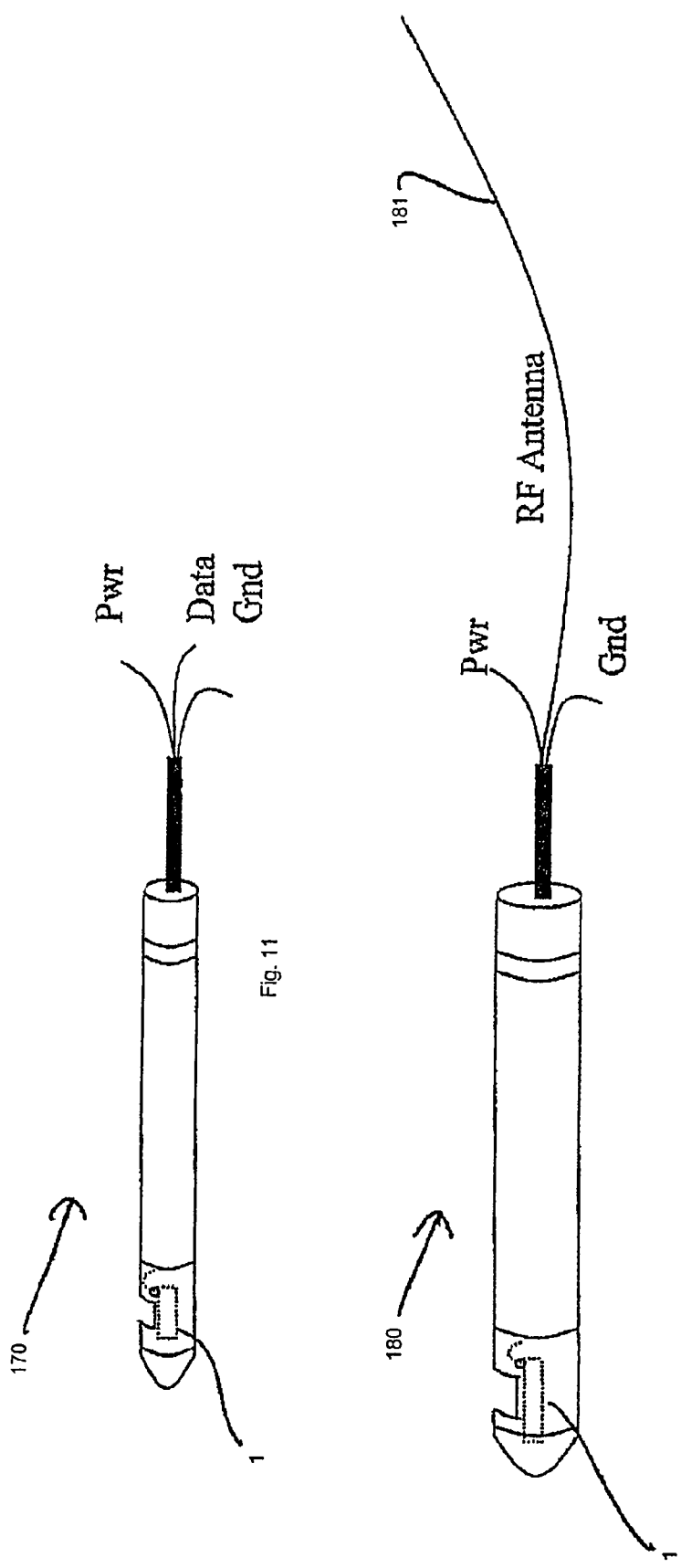

INTEGRATED CMOS POROUS SENSOR

This patent application is a continuation-in-part of U.S. patent application Ser. No. 12/453,965, filed May 28, 2009 which is a divisional of U.S. patent application Ser. No. 11/092,725, filed Mar. 30, 2005, now U.S. Pat. No. 7,554,134, which claims priority of U.S. Provisional Application Ser. No. 60/558,565, filed Apr. 2, 2004, all of which are incorporated herein by reference in their entirety. This application is also a continuation of U.S. patent application Ser. No. 11/992,470, filed Mar. 24, 2008 now U.S. Pat. No. 8,007,167 which claims priority as a national stage application of PCT/IE2006/000107 filed Oct. 2, 2006 which claims priority to U.S. Provisional Application Ser. No. 60/721,968, filed Sep. 30, 2005 all of which are incorporated herein by reference in their entirety.

INTRODUCTION

1. Field of the Invention

The invention relates to electronic sensors.

2. Prior Art Discussion

One of the main driving forces in the electronics industry is the desire to achieve greater integration of functionality so that production is more automated, and size and per-unit cost reduced. Most importantly, for battery applications, higher integration generally results in lower power, due to reduced parasitic capacitances.

However the continual shrinking of CMOS transistors means that gate delays are reducing, so that overall delays are now becoming dominated by interconnect delay, especially due to the resistivity of Aluminium and capacitance of silicon dioxide ($SiO_2$, dielectric constant K=4 approx). In the field of sensors, and in particular wireless sensors, greater integration has been slow because of the difficulties encountered in integration of microcontroller, A-to-D converter (ADC), EEPROM memory, RF transceiver, and sensor elements in the one integrated sensor device. These difficulties have arisen because of incompatibilities of materials processing for the various elements. For example, sensor elements have conventionally been manufactured on ceramic or glass substrates and cannot be easily integrated on silicon. It has also been difficult to integrate RF transceivers, EEPROM/Flash EEPROM memories, and mixed-signal converter circuits on a single CMOS chip, due to the different processes required—bipolar transistors, floating-gates, and poly-poly capacitors, which suffer from substrate parasitics, strain, and mis-match effects. Also, the aluminium metallisation used in IC processing is prone to corrosion, thus limiting usefulness for some types of sensor applications.

U.S. Pat. No. 6,724,612 and U.S. Pat. No. 6,690,569 describe sensor devices having both electronic and sensing components, the latter being capacitive electrodes. However, the electrodes require platinum or gold coating, spray or print deposition of a proprietary polymer as a moisture-sensing dielectric, and laser trimmig for some circuits. This processing is not amenable to high-volume semiconductor processing, since these are non-standard materials (or even regarded as contaminants) in a modem CMOS fabrication plant. Therefore they are typically applied in a specialist fabrication plant, or a post-processing operation in a specialist facility, leading to extra cost and production bottlenecks.

The invention addresses these issues.

SUMMARY OF THE INVENTION

According to the invention there is provided an integrated sensor device comprising:

MOS circuits in a semiconductor substrate, interconnect levels each with interconnect conductors and insulating dielectric, said levels being over the substrate and interconnecting the MOS circuits, said interconnect conductors including sensor electrodes and said interconnect dielectric including a Low-K dielectric material as a sensor dielectric material for absorption of gas or humidity to be sensed, and the MOS circuits include a processor for processing signals from the sensor electrodes to provide a gas or humidity output.

The sensor dielectric preferably comprises an organic polymer.

There are enormous advantages to integrating manufacture of the sensor electrodes and dielectric into the MOS interconnect level manufacture, and to using a Low-K dielectric with an organic polymer instead of being only an oxide. It has been found that such a dielectric allows sufficient ingress of gas or moisture and a good response characteristic.

In one embodiment, the sensor dielectric material is of a type which thermosets with sufficient free space volume for gas or humidity sensing when cured. Such materials are particularly effective for not only low-temperature deposition in a MOS process, but are excellent as sensor dielectrics.

In one embodiment, the sensor dielectric material is hydrophobic. This allows fast egress of the small quantity of gas or humidity which ingresses In one embodiment, the sensor dielectric material has a moisture uptake level of less than 0.5%.

In one embodiment, the sensor dielectric is a polyimide.

In one embodiment, the sensor dielectric comprises a cross-linked polymer.

In one embodiment, the sensor dielectric has spin-on deposition properties.

In one embodiment, the sensor dielectric comprises a sol-gel $SiO_2$ composition.

In another embodiment, the processor comprises an A-to-D converter connected between the sensor electrodes and the processor and having a precision of at least 8 bits, and preferably at least 16 bits, and in on embodiment 18 bits.

In one embodiment, the A-to-D converter comprises an array of dummy capacitors with a constant topography surrounding active A-to-D converter capacitors.

In one embodiment, the sensor is a capacitive sensor.

In a further embodiment, the device comprises a passivation layer protecting at least some MOS circuits.

In one embodiment, the sensor electrodes comprise reference electrodes under the passivation layer and sensing electrodes over the passivation layer.

In one embodiment, the sensor comprises etch stop layers between the interconnect levels, and the passivation layer is of the same composition as the etch stop material.

In one embodiment, the passivation layer is of $Si_3N_4$ composition.

In a further embodiment, the passivation layer is recessed over the sensing electrodes.

In one embodiment, there is sensor dielectric material in the recess.

In one embodiment, at least some of the sensor dielectric is between the electrodes and is exposed.

In one embodiment, the MOS circuits are directly beneath the sensor in a vertical dimension.

In one embodiment, the MOS circuits include a temperature sensor.

In one embodiment, the temperature sensor comprises a PNP transistor in the interconnect layers.

In another embodiment, the MOS circuits include a microcontroller for processing signals from the sensor and temperature signals from the temperature sensor to provide an enhanced output.

In one embodiment, the enhanced output includes temperature-corrected gas or humidity readings.

In one embodiment, the sensor further comprises a light emitting diode.

In one embodiment, said diode is formed in a deep trench to a lower interconnect level laterally of the sensor electrodes.

In one embodiment, the device comprises a photo-detector diode.

In one embodiment, said diode is in a deep trench in a lower interconnect level laterally of the sensor electrodes.

In one embodiment, the MOS circuits include a wireless transceiver.

In one embodiment, the wireless transceiver is for communication with other nodes in a network, and it comprises a means for switching channel frequency according to a low frequency channel switching scheme upon detection of interference.

In one embodiment, the sensor comprises an interconnect level including a low noise amplifier.

In one embodiment, the low noise amplifier comprises a MOS device with its channel region formed in a strained silicon region beneath a poly gate.

In one embodiment, the sensor comprises a detecting element connected between pads on an upper surface of the device.

In another aspect, the invention provides a method of producing any sensor device defined above, the method comprising the steps of: fabricating the MOS circuits in the substrate, fabricating the interconnect levels in successive fabrication cycles according to interconnect design to interconnect the MOS circuits, and fabricating the sensor electrodes and dielectric in a final interconnect level in an integrated process.

In one embodiment, the method comprises the further step of depositing a passivation layer over a top interconnect level.

In one embodiment, the method comprises the further steps of depositing an etch stop layer over each layer of dielectric in the interconnect levels, and depositing etch stop material over the top interconnect level dielectric to provide the passivation layer.

DETAILED DESCRIPTION OF THE INVENTION

Brief Description of the Drawings

The invention will be more clearly understood from the following description of some embodiments thereof given by way of example only with reference to the accompanying drawings in which:

FIGS. 5 to 8 are cross-sectional views of sensing parts of alternative sensor chips of the invention;

FIG. 9 is a diagram showing chip encapsulation;

FIG. 10 is a plan view and a diagrammatic side view showing an RFID tag incorporating the chip of the invention;

FIGS. 11 and 12 are perspective views of probes incorporating chip sensors of the invention;

FIG. 13 is a circuit diagram of a 12-bit SAR A-to-D converter of the sensor device, and FIG. 14 is a layout view of the capacitor array for the SAR converter;

DESCRIPTION OF THE EMBODIMENTS

Figure 1:
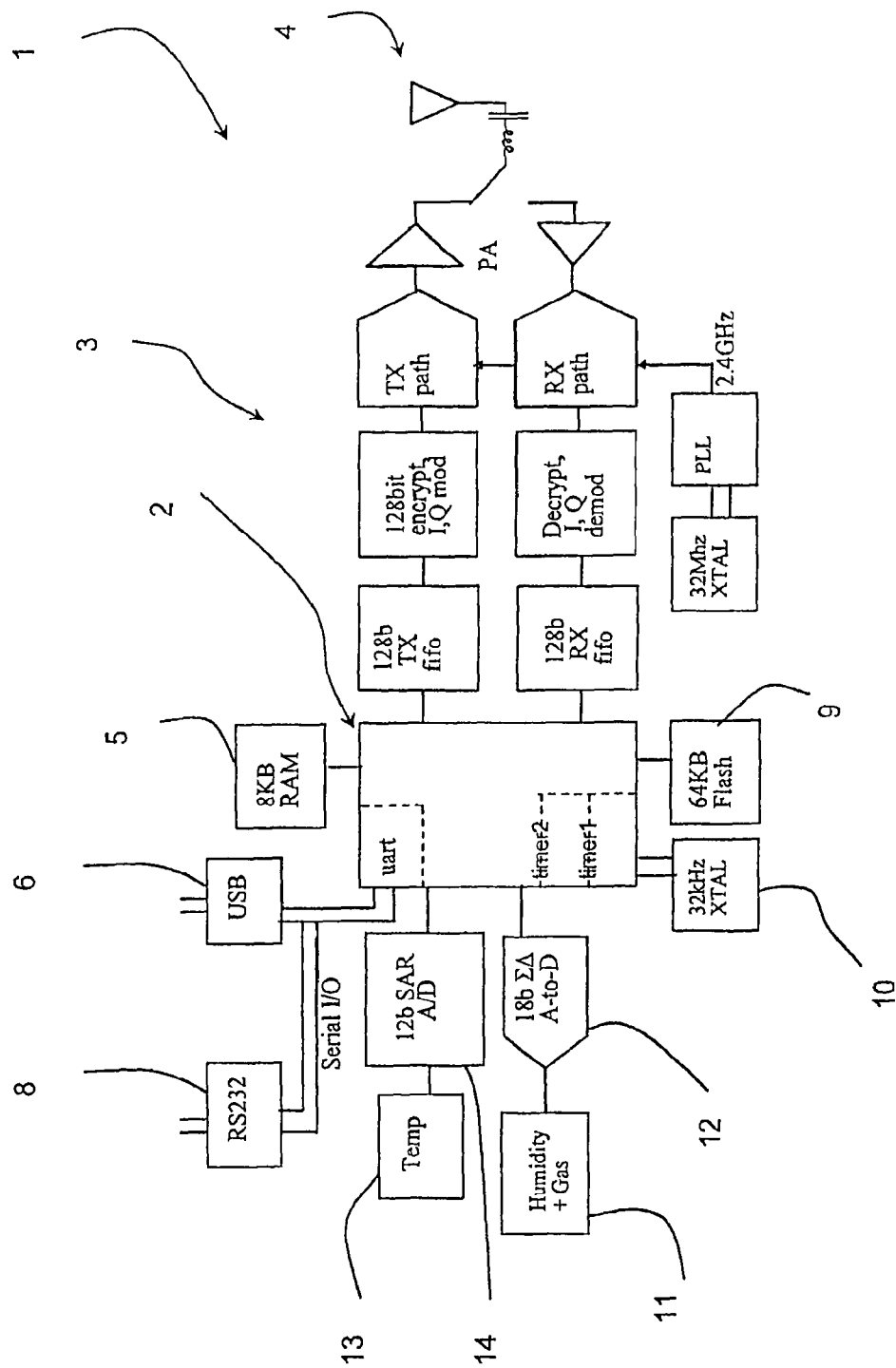
FIG. 1 is a block diagram of an integrated sensor chip of the invention.

A single chip wireless sensor 1 comprises a microcontroller 2 connected to a transmit/receive interface 3, which is coupled to a wireless antenna 4 by an L-C matching circuit. The microcontroller 2 is also connected to an 8 kB RAM 5, a USB interface 6, an RS232 interface 8, 64 kB flash memory 9, and a 32 kHz crystal 10. The device 1 senses humidity and temperature, and a humidity sensor 11 is connected by an 18 bit $\Sigma\Delta$ A-to-D converter 12 to the microcontroller 2 and a temperature sensor 13 is connected by a 12 bit SAR A-to-D converter 14 to the microcontroller 2.

The device 1 is an integrated chip manufactured in a single process in which both the electronics and sensor components are manufactured using standard CMOS processing techniques, applied to achieve both electronic and sensing components in an integrated process.

Figure 2:
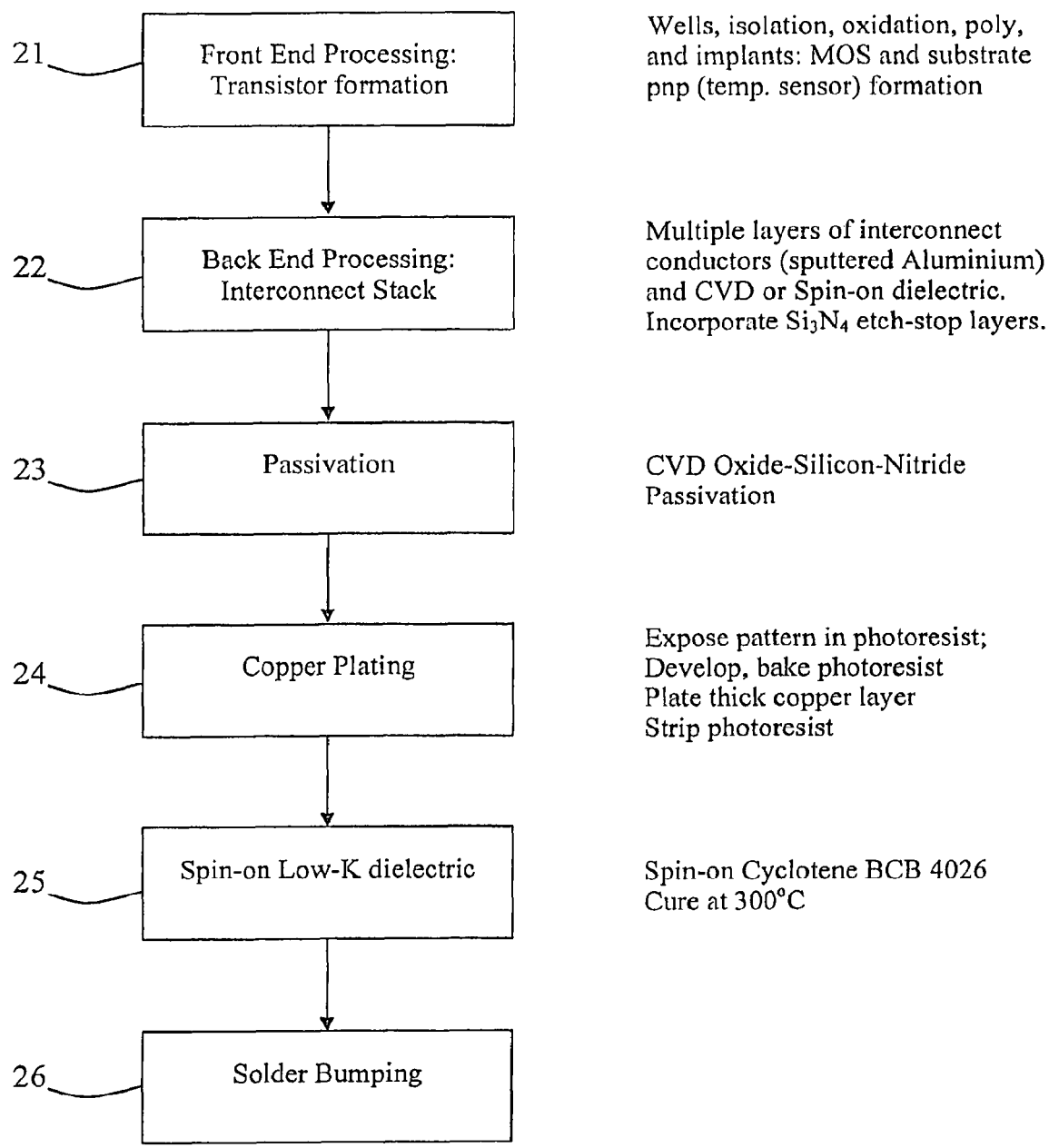
FIG. 2 is a flow diagram illustrating a production method for the chip.
Figure 3:
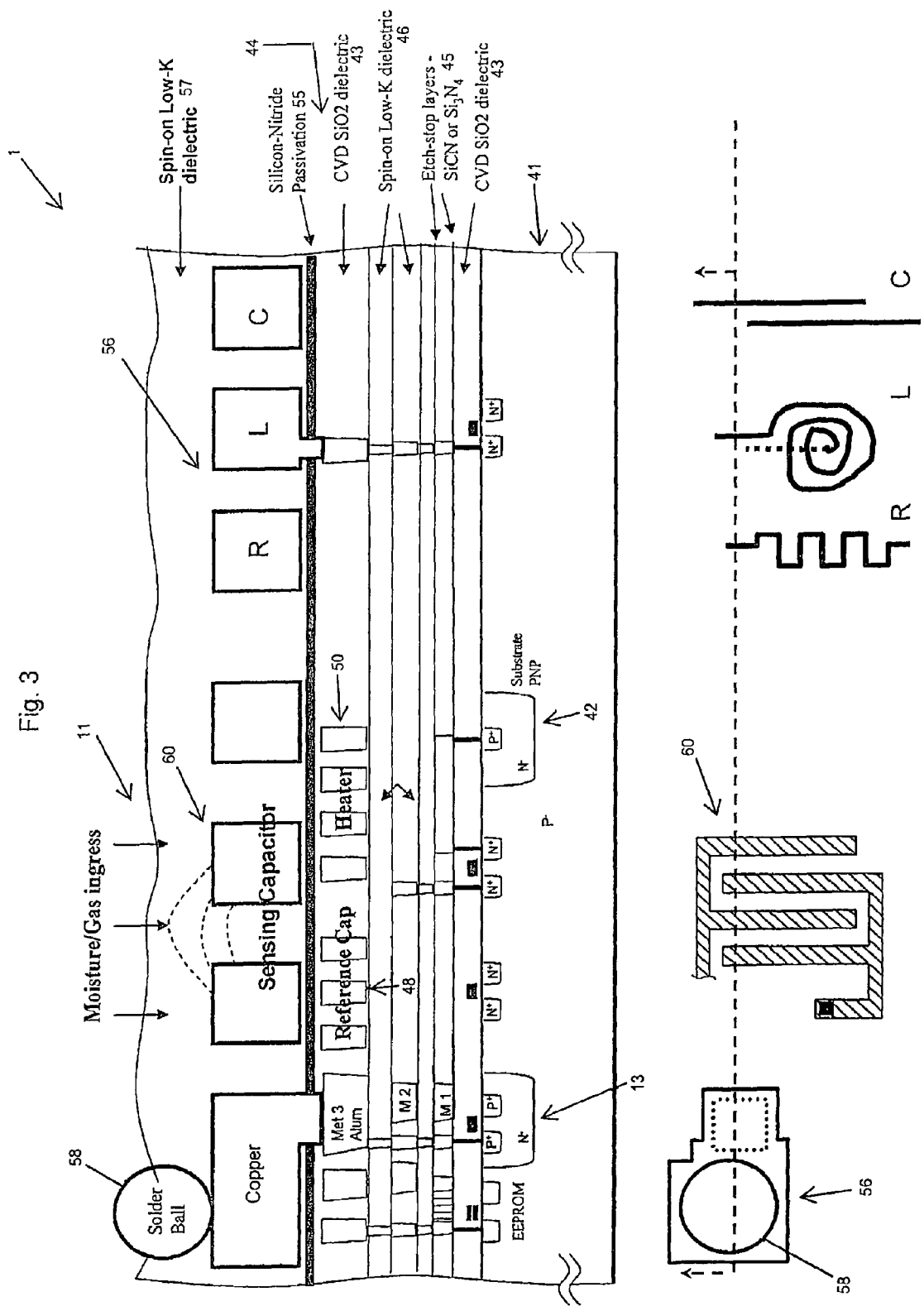
FIG. 3 is a diagrammatic cross-sectional representation of the sensor chip together with some plan views of parts of the chip.
Figure 4:
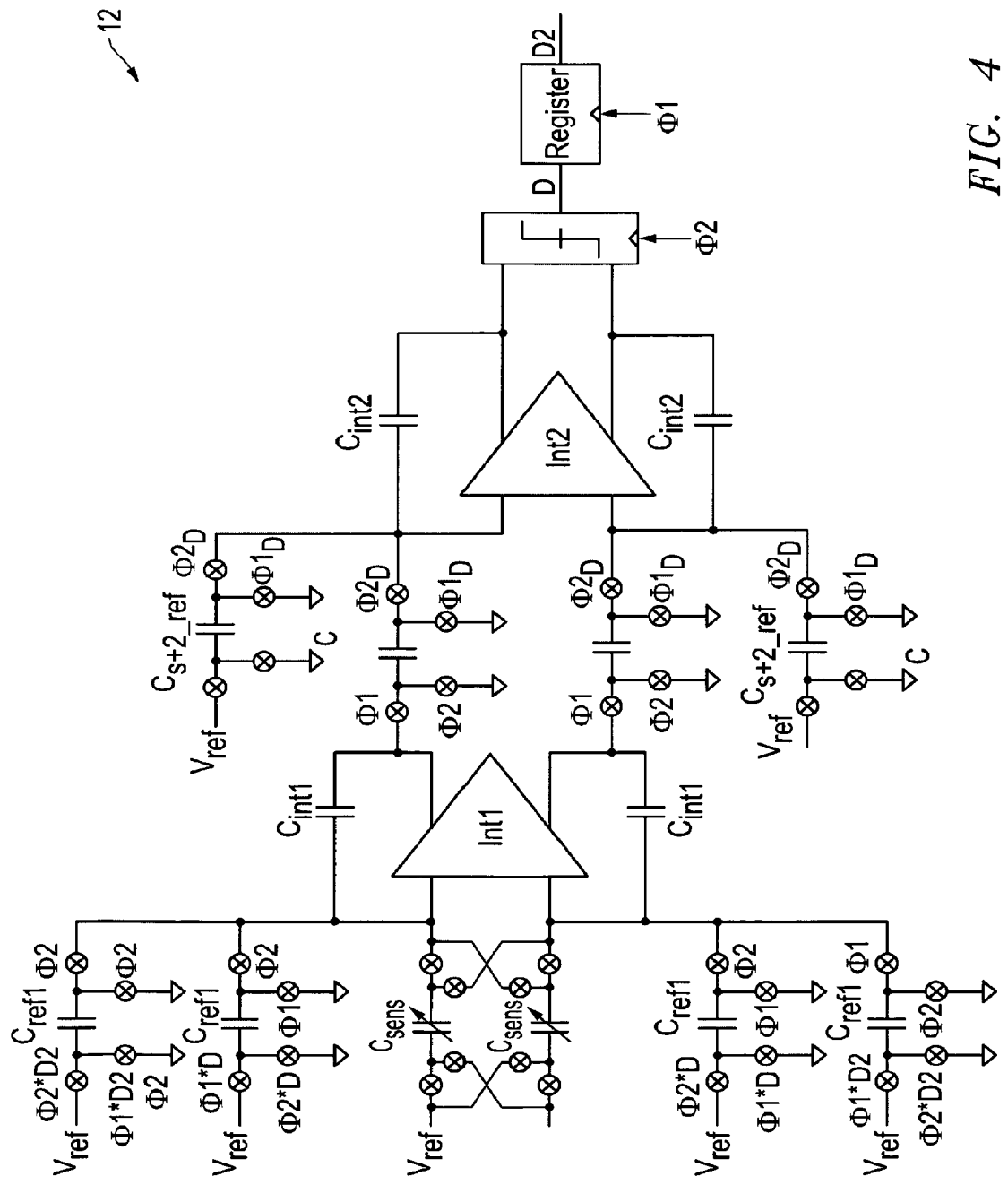
FIG. 4 is a circuit diagram of an 18-bit A-to-D converter of the chip.

The manufacturing process 20 is now described in more detail referring to FIGS. 2 to 4, and the steps are 21 to 26 inclusive.

Front End Processing

A substrate 41 of silicon is processed to form CMOS wells, isolation oxidation, poly-silicon gates, and implants to form MOS and EEPROM components 42, as is well known in CMOS processing. Also, in the substrate a temperature-sensitive PNP transistor is formed to provide the temperature sensor 13.

Back End Processing

Tungsten contact plugs and silicon dioxide insulating dielectric 43 are deposited by Chemical Vapour Deposition (CVD). Aluminium is then sputtered onto the wafer and etched, forming a first metal interconnect layer (M1). The sequence of dielectric-deposition, metal sputter and etch is then repeated several times, forming a stack 44 of interconnect layers, typically five to nine metal layers on deep submicron CMOS processes. However, only four metal layers are shown in FIG. 3 for clarity. Each cycle finishes in deposition of an etch stop layer 45 for limiting the extent of etching in the next cycle. The etch stop material is silicon nitride $Si_3N_4$.

Low-K dielectrics are also used in the CMOS interconnect stacks because they enable lower capacitance for faster signal transfer between components. K is the relative permittivity or dielectric constant, and is typically 3.9 for $SiO_2$. The following are some examples of some Low-K materials used:

TABLE 1

| Materials | Application | k value |
| --- | --- | --- |
| Fluorosilicate glass (FSG) | CVD | 3.2-4.0 |
| Polyimides | Spin-on | 3.1-3.4 |
| Hydrogen silsesquioxane (HSQ) | Spin-on | 2.9-3.2 |
| Black Diamond ™ (SiCOH) | CVD | 2.7-3.3 |
| B-staged Polymers (CYCLOTENE ™ & SiLK ™) | Spin-on | 2.6-2.7 |
| Fluorinated Polyimides | Spin-on | 2.5-2.9 |
| Methyl silsesquioxane (MSQ) | Spin-on | 2.6-2.8 |
| Fluorinated DLC | CVD | 2.4-2.8 |
| Parylene-F | CVD | 2.4-2.5 |
| Aerogels/Xerogels (porous silica) | Spin-on | 1.1-2.2 |

FIG. 3 is a cross-sectional diagram of the device 1, showing the substrate 41 with CMOS components 42, and showing the interconnect stack 44 beginning and ending with "regular" $SiO_2$ 43, for mechanical strength. However the intermediate dielectric layers 46 are "Low K", in this case a spin-on Low-K (SiLK) resin. It may alternatively be a low-K porous silicon dioxide layer.

The top aluminium layer M3 includes a heating element 50 with an internal temperature monitor for instantaneous heating and purging of the humidity sensor 11 with immediate temperature monitoring. Also, at this level, the process includes a thin metal plate for a capacitor top metal (CTM) with a thin layer (0.04 μm) $SiO_2$ dielectric between CTM and one of the Aluminium interconnect layers, forming mixed signal metal-insulator-metal (MIM) capacitors for both of the A-to-D converters. The metal plates result in a much lower voltage coefficient of capacitance than poly-poly capacitors, making MIM capacitors much more amenable to high quality RF and A-to-D converter circuits. The metal layer M3 also includes a reference capacitor 48.

Passivation 23:

A sandwich of silicon dioxide and silicon nitride is deposited by CVD to form a passivation or protection layer 55. A well-known feature of silicon nitride is its strength and imperviousness, so it acts as an excellent barrier to moisture and contaminants which might enter the chip, and it provides excellent protection for the reference capacitor 48 and all of the components in the interconnect layers 44 and the CMOS components beneath.

Copper Plating 24, Spin-on Low-K 25, and Solder Bumping 26

Taking advantage of the barrier properties of Silicon nitride, a layer 56 of thick copper is formed on top of the chip, enabling high-quality resistors, inductors, and capacitors to be implemented "on-chip", for example the L-C antenna matching circuit of FIG. 1, the L-C tank in an on-chip synthesizer VCO, or 50 Ohm termination resistors. The process involves pattern exposure in photoresist, then developing and baking the photoresist, plating the thick copper layer in the photoresist 'trenches' to a thickness of 5 μm, and finally stripping photoresist. Then polyimide Low-K material 57 is spun onto the wafer, at 1500 RPM to a height of 10 μm, and cured at 300° C. This temperature is much lower than CVD temperatures of 400-600° C., an important factor in stacking multiple interconnect levels on a modem MOS process where transistor junction depths are quite shallow, and may be at risk of 'drive-in' by too much high-temperature processing in the back-end dielectric layer additions. The polyimide Low-K material when cured becomes thermoset, and the lower mass-to-volume ratio results in K, its dielectric constant, reducing to 2.9. This K value, is a 25% drop in capacitance compared to $SiO_2$, This, together with the lower resistance of the thick copper layer, results in much higher Q-Factor for the copper inductors, and much lower interconnect delay. The thermoset dielectric, while not regarded as porous in the conventional sense, has sufficient free space volume to admit enough gas or humidity for sensing.

In general terms, it has been found that a dielectric which is "Low-K" and comprises an organic polymer also has advantageous properties for allowing ingress of gas or humidity, even though the process of making the material "Low-K" had the aim of achieving the enhanced electrical properties. Also, we have found that if the Low-K material is of the type having a cross-linked polymer which thermosets when cured the sensor dielectric properties are particularly advantageous. These materials offer good resistance to chemicals and solvents and therefore there has been a perception in the industry that they act as a barrier and protection against moisture or other fluids. However, we have found that there is sufficient ingress of gas or moisture to act as a good sensor dielectric, with a linear response. The following is a table of capacitance vs. relative humidity readings for a Cyclotene-BCB 4026 Low-K dielectric, which may be used instead of the polyimide dielectric.

| Humidity | Capacitance | % Capacitance change |
| --- | --- | --- |
| 20 | 32.06 | 0 |
| 30 | 32.07 | 0.031191516 |
| 40 | 32.09 | 0.093574548 |
| 50 | 32.11 | 0.15595758 |
| 60 | 32.14 | 0.249532127 |
| 70 | 32.18 | 0.374298191 |
| 80 | 32.25 | 0.592638802 |
| 90 | 32.31 | 0.779787898 |

Figure 3A:
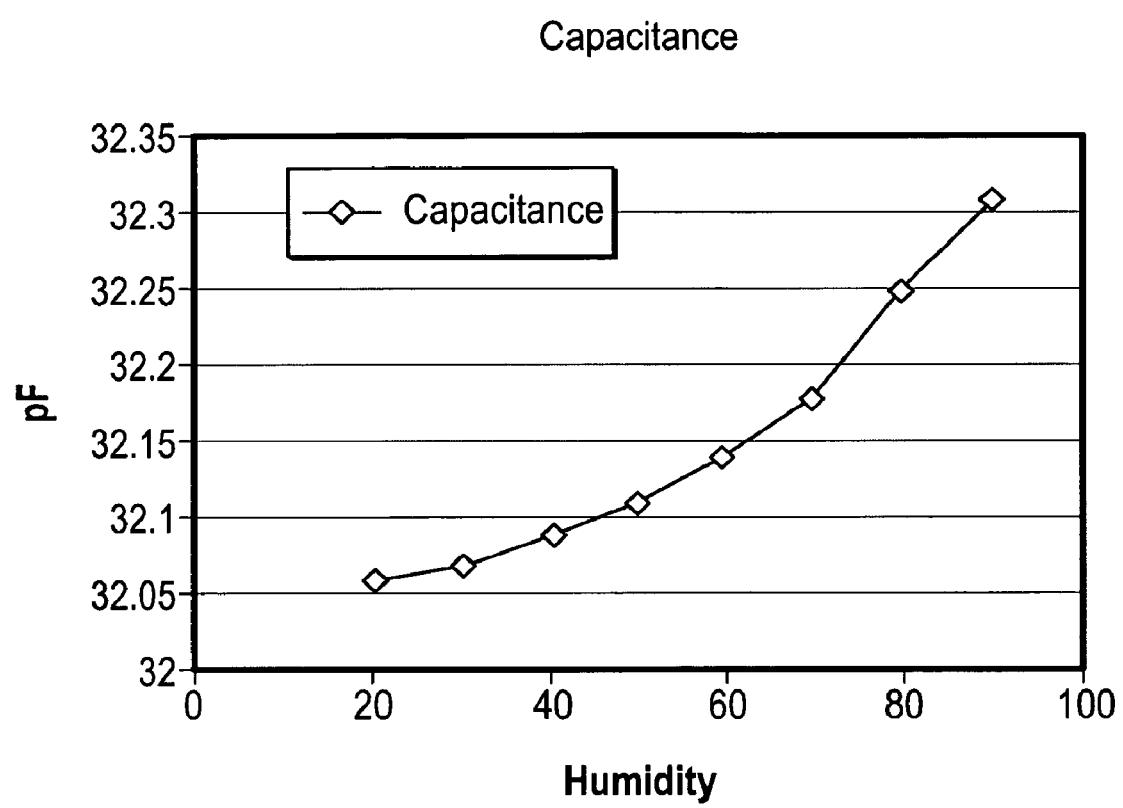
FIG. 3A is a graph of capacitive vs. relative humidity readings.

A graph of the capacitance vs relative humidity readings is shown in FIG. 3A.

We expect broadly similar characteristics for other Low-K dielectric materials with organic polymers, such as those of polyimide and sol-gel. Finally, openings are etched in the polyimide, in which solder balls 58 are formed on the copper pad connections to complete the step 26. This enables the chip to be soldered directly to a circuit board ("flip-chip") without the use of bond-wires. This results in very low inductance and resistance in the I/O connections. This is important for RF circuits and for low current battery operation.

Another example of a Low-K material is MCM 41/33, a sol-gel $SiO_2$ which is spun-on at room temperature. The dielectric $SiO_2$ layer is formed by applying a droplet of 1 ml of the sol-gel. This is spun on at wafer spin speed of 500 RPM for 10 seconds. This is followed by a cure at 70° C. for four hours and a calcination cycle at 300° C. to drive out solvent surfactants. The result is a porous Low-K sol-gel $SiO_2$ dielectric layer with hexagonal pores of diameters in the region of 2 to 10 nanometers, resulting in a low K value of 2.7 approx.

In another example, the sensor dielectric comprises Black Diamond (SiCOH), in which carbon doping breaks up an $SiO_2$ lattice, making it porous and thereby reducing its capacitance.

Moisture or some gases can ingress into the Low-K materials due to their free-space volume. This ingress results in a change of conductivity and/or dielectric constant. The high-resolution A-to-D converter 12 co-located on the same chip measures these changes, resulting in a humidity and/or gas sensor, formed in the interconnect layers.

The hydrophobic nature of some Low-K materials such as polyimide and BCB Low-K materials means the resulting change can be quite small, for example less than 0.5% moisture uptake. An advantage of the hydrophobic property is quick egress of moisture, giving a fast response time, with no requirement for heater purge cycles (which would be detrimental to long battery lifetime and reliability). The small pore sizes also mean very little contaminants entering the Low-K material, resulting in a very reliable sensor. The hydrophobic properties also mean that there is a very low chance of contaminants reaching the electrodes.

The 0.5% moisture uptake is quite low, but is detectable by the embedded co-located 18-bit A-to-D converter. This is achieved by forming a sensing capacitor 60 in the copper layer above the silicon-nitride passivation layer 55, and forming an equal value reference capacitor 48 beneath the silicon-nitride in one of the aluminium interconnect layers. The barrier properties of the silicon-nitride passivation 55 prevent moisture ingress to the reference capacitor 48, so that these capacitances form the differential front-end of a second-order over-sampled sigma-delta modulator, where the small capacitance difference represents the relative humidity signal. This provides a high level of integration between the sensor and converter components.

Take for example a 0.5% change in sensing capacitance as the ambient atmosphere varies from zero to 100% humidity: Since the sensor capacitor is part of a switched-capacitor circuit, it will switch between the reference voltage 1.22V and ground, the effective input signal is: 1.22*0.5%=6.1 mV. To measure the humidity to 0.5% accuracy, means that the ADC must be able to measure 6.1 mV*0.5%=30.5 uV. However, to ensure that the ADC isn't bouncing between values, the RMS noise floor needs to be one sixth of this, 30.5 uV/6=5 uV. Therefore the actual noise floor needs to be 5 µV, while the full input will be 1.22V. This corresponds to 18-bit resolution. FIG. 4. is a schematic of the sigma-delta converter 12, consisting of a second-order fully differential over-sampling architecture, with chopping of the sensing capacitors and input stage. Very high resolution is achieved by trading off the number of samples per second and over-sampling ratio using the decimation filters.

As an integral part of plating the top interconnect layer humidity-sensing capacitive interdigitated fingers (electrodes) 48 are formed. The size and spacing of the fingers is chosen to suit the application. In this embodiment the fingers 48 have a width of 15 µm and a spacing of 15 µm. Using cyclotene (BCB, permittivity K of 2.6) and for a capacitor structure of 2.0×2.0 mm and a copper thickness of 9 µm this gives a sensor capacitance value of 9.7 pF.

It will be appreciated from the above that standard Deep-Sub-Micron CMOS processing techniques and materials are used, thus achieving fully integrated production. The sensor electrodes are made simultaneously with the rest of the chip, using the same dielectric and metal layers as used for interconnect and RF inductor and capacitor components. This 'standard CMOS' method is very advantageous to the high-volume manufacturability of this sensor 1.

This approach has not apparently been attempted heretofore because of the perception that such a sensor would require gold or platinum plating and/or other non-standard materials which would be regarded as contaminants in a modern CMOS wafer fabrication plant. In this invention the sensor takes advantage of developments in processing with Low-K dielectric materials in the semiconductor industry for their desirable dielectric properties and low-temperature process deposition. The invention benefits from the allowance of ingress of small quantities of moisture, and also from the hydrophobic nature of the material.

In use, moisture ingresses into the film 57 so that it affects its dielectric constant between the sensing fingers 60. The results are given in the table and plot above.

Humidity variations of 1% or 2% now produce capacitance variations of less than a femtoFarad—still detectable by the highly over-sampled differential sigma-delta high-resolution converter 12. 18 bits of resolution also provides a very large dynamic range, enabling the converter to easily cope with the highly variable and non-linear capacitance-versus-humidity characteristics of different oxides and different pore sizes from wafer to wafer and lot to lot.

The Low-K material may alternatively be deposited by CVD or 'ink-jet/drop-on-demand' or print-on methods, eliminating extra etching steps.

In another embodiment, a polyimide mask may include an extra opening to eliminate polyamide from over a reference capacitor. Since polyimide is porous, the portion over the sensing capacitor now experiences a minute change in capacitance versus humidity.

Referring to FIG. 5, in this embodiment a low-K dielectric material is used in a top dielectric layer 100 only. The sensor device therefore has a low-K dielectric material between capacitive interdigitated fingers 101 forming a reference capacitor and fingers 102 forming a sensing capacitor. By placing a 'dummy' bond pad passivation opening 103 over the sensor structure, the surface above the sensing fingers 102 is exposed for ingress of moisture into the dielectric between the fingers during the bond-pad etch. This leaves passivation 104 over the full area except the sensing capacitive fingers 102.

FIG. 6 illustrates a variation having 'regular' silicon dioxide dielectric layer 110, and parts similar to those of FIG. 5 have the same reference numerals. This embodiment has the advantage of using the standard commodity CMOS process with no extra masks and no extra processing steps required. However, it allows access by the moisture to the capacitive fingers 102 as an air-dielectric, with a K value of 1.0. For some applications this is not a problem, for example a moderate-humidity office environment where the sensor electrodes only experience a few milliVolts applied for a few milliseconds once every few minutes. The risk of electrolytic corrosion of aluminium or copper electrodes is low in this scenario. Even if the bond pad etch is over-etched, which would remove some or all of the dielectric, the sensor would still work even with air as a dielectric.

FIG. 7 shows a variation in which spin-on polyimide 120 flows into the dummy bond pad opening 103. This now has the advantage of protecting the aluminium from direct air exposure, while the polyimide 103 also acts as a humidity sensing element as described above.

FIG. 8 shows an arrangement in which there is an opening 130 in polyimide 131 over reference electrodes 132. However, the polyimide overlies sensing electrodes 133, so that the sensor electrodes sense the fringe field.

FIG. 9 shows a simple potting arrangement for enclosing the single-chip wireless sensor 1. The sensor 1 is bonded to a coin battery 140 by conductive grounding adhesive 141 and there is encapsulation 142. A metal clip supplies power to the chip from the underside of the battery, and 0402 surface-mount crystals are attached to copper pads on the chip surface. These pads are designed to withstand several kg pull force, and solder-bumping of the pads is now common in Deep Sub Micron CMOS chips, making the pads amenable to attachment of timer and RF crystals. A former is used to keep the area over the sensing component clear. All other areas are enclosed by the encapsulant 142, which affords physical protection, as well as protection of the chip and battery terminals from corrosion or electrolytic degradation if exposed continuously to high moisture environments. No metal is exposed, anywhere, except for an RF antenna wire 1433.

Alternatively, there may be no encapsulation if physical protection is less important and/or if response time to temperature variations is more important.

The high level of integration of this single-chip wireless sensor makes it suitable for the RFID market, where high integration and low cost are key features. By encasing the chip in any of the porous polymer layers listed in the Table above, it becomes a single-chip RFID temperature-humidity sensor.

FIG. 10 shows another packaging arrangement for the single-chip wireless sensor 1, in this case as an active RFID tag 149. The solder-bumps enable the chip 1 it to be mounted directly on a flexible polyimide carrier 150. It is sealed by a polymer layer 151 on top. An antenna 152 is formed in the polyimide carrier, along with connections to a coin-battery by etching and plating. In addition, interdigitated capacitor structures 153 are formed in this polyimide carrier. These make use of the Low-K characteristic of the polyimide to measure humidity variation, relative to the reference capacitor in the chip which is protected from variation by the silicon nitride passivation layer. The package is the sensor, resulting in a simple and inexpensive single-chip RFID temperature & humidity sensor, where the sensing element is in the same dielectric as the RF inductors and interconnect.

Temperature Sensors

In addition to the metal heater temperature sensor described above, a substrate PNP temperature sensor 13 is also developed as an integral part of the substrate 41, as shown in FIG. 3. This relies on the well-known −2.2 mV/° C. Vbe characteristic of the base emitter junction. By having a combination of humidity and temperature sensors in the one device, there can be calculation of an enhanced reading by the microcontroller, namely dew point. These, together with the microcontroller 2 and the flash memory 9 allow use of look-up tables for scaling and calibration, to achieve accuracy to within 0.5° C.

In a 0.18 um CMOS process, the size of the chip 1 is small enough that it can be mounted directly in various standard probe fittings such as a humidity probe 170 or a temperature-humidity RF probe 180, as shown in FIGS. 11 and 12 respectively. The single-chip integration means the probe gives a direct digital output, so no further electronics are required. In the probe 180, data is communicated by RF on an antenna wire 181, enabling this probe, in-situ in its measurement location, to become part of a wireless-mesh network, eliminating the cost of wiring the sensor back to a control station.

Referring to FIG. 13, the 12-bit SAR converter 14 is shown. This measures the Vbe voltage of the PNP, or the temperature-dependent resistance of the metal heater monitor in a bridge configuration as shown. The converter achieves 12 bit resolution without any calibration circuits, as follows. Referring to FIG. 14 the capacitor array for the converter 14 is in the center of the level, and it is surrounded by eight similar dummy arrays 190 to ensure constant topography and excellent matching of the key array capacitors in the converter 14. The array is segmented into 7 upper bits and a 5-bit sub-DAC via coupling capacitor Cc. This, together with a small unit capacitor size of 7×7 mm, keeps the entire array capacitance (Cs) at around 8 pF, small enough that it can be driven efficiently with an on-chip buffer amplifier as shown, and also small enough that global mismatches due to gradients in oxide thickness or other process parameters are minimized. At a sampling frequency of 100 KHz, the kT/C noise figure is 140 nV, well below the 12-bit LSB size being on Metal 5 (fifth level), the capacitors have very small parasitic capacitances to the substrate, simplifying matching of the ratioed capacitors. The Metal-Insulator-Metal (MM) structure of these capacitors results in low voltage and temperature coefficients and parasitic resistances.

The typical analogue voltage ranges are less than 1V, since the maximum allowable voltage on deep-sub-micron CMOS processes is low, for example 1.8V or 1.2V (on 0.18 um and 0.13 um CMOS respectively). Most of these processes have a thicker oxide (typically 70 angstrom) to facilitate a 3.3V I/O transistor capability. These transistors may be used for the input track-and-hold, and other critical sections of the A-to-D converters, where headroom and noise floor are limiting factors. These factors are constant, therefore if the analog signal swing can be doubled or quadrupled, e.g. from 0.6V to 1.2V or 2.4V, this represents a 3 dB or 6 dB improvement in converter performance, respectively.

Flash Microcontroller

Having the 8-bit microcontroller 2 and the 64 KB Flash memory 9 on the same chip as the sensor enables significant improvements in accuracy and functionality. This is because real-time continuous calibration or in-situ calibration over various conditions of temperature is achieved. This amount of memory is also sufficient to accommodate the entire IEEE802.15.4 protocol and Zigbee software stack to perform beacon, peer-to-peer, star and mesh networking, key requirements of modern wireless sensor networks. An on-chip regulator generates 1.2V, which powers most of the microcontroller, memory blocks, and wireless RF transceiver, which are fabricated on thin-oxide (e.g. 28 angstrom) minimum geometry devices.

Figure 15:
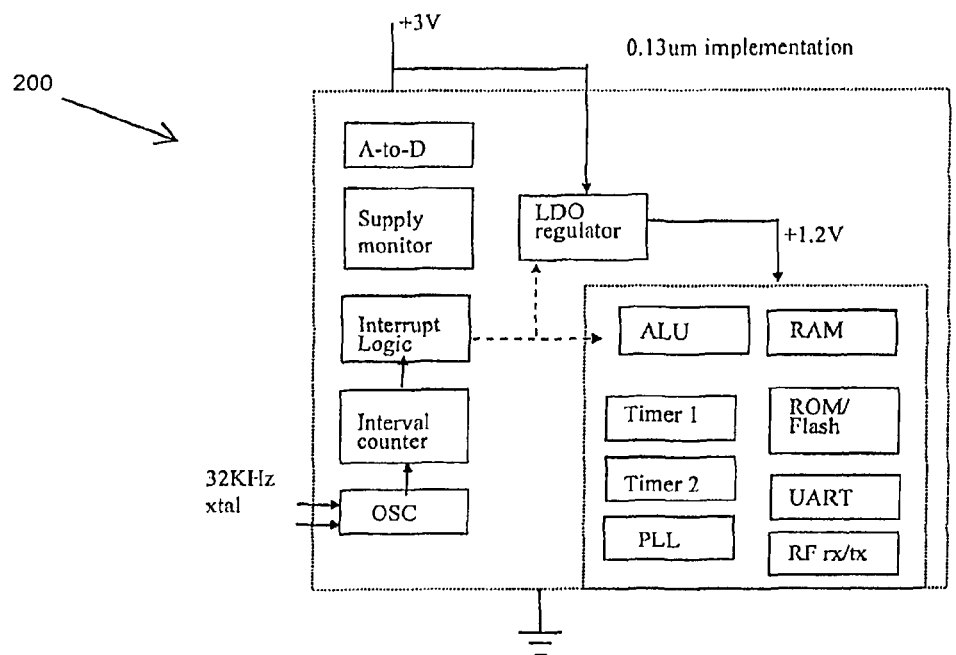
FIG. 15 is a block diagram of a microcontroller of the device.

To facilitate lower power, the time-interval counter and part of the microcontroller's interrupt logic 200 is implemented on thick-oxide 3.3V transistors, as shown in FIG. 15. This means the regulator can be switched off when the chip is in sleep or power-down mode, eliminating the DC bias currents of the regulator. This, together with almost-zero sub-threshold leakage of the 3V transistors, results in significant power saving and elongation of battery life. On wakeup from power-down, for example after the time-interval-counter counts a delay of several minutes, the microcontroller achieves reduction of noise and substrate crosstalk by operating the sensors, converters, and radio transceiver sequentially. Thus the LNA receiver achieves higher Signal-to-Noise (SNR) and the A-to-D achieves higher accuracy due to the microcontroller being halted at those particular instants. This event-driven sequential nature of operation is encapsulated in a low-power operating system (OS) which is almost entirely interrupt and event-driven, simplifying the OS software and memory requirements significantly, a very important criteria for cheap low-power wireless sensors. The sequential operation also reduces peak current demand from the battery, further elongating its useable lifetime to several years.

Figure 16:
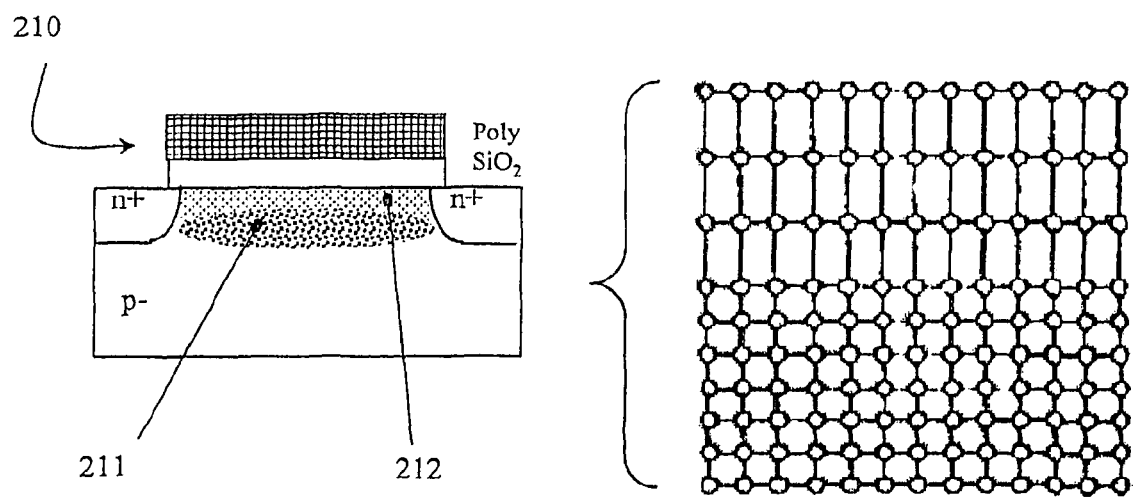
FIG. 16 is cross-sectional diagram showing a sub-surface current flow path in a strained-silicon transistor of the device.

Turning now to the wireless transceiver 3, and its low noise amplifier (LNA) in particular, the LNA is designed to have extra low power and low noise operation. This is enabled by copper inductors on the fifth or sixth interconnect levels, (i.e. same top metal layer which forms the sensor electrodes), and the use of strained silicon MOS devices 210 for the front-end LNA, see FIG. 16. This diagram shows a thin layer of Silicon-Germanium 211, over which there is a thin strained silicon layer 212, with higher carrier mobility than regular silicon. The polysilicon gate 210 creates a channel in the strained silicon region. However the majority of the transistor current flows in the sub-surface SiGe region due to the higher mobility of Germanium, giving lower noise operation (due to less electron trapping at surface interface states), and higher gain. The LNA can therefore be biased at lower currents for the same gain, saving battery power. Copper has lower resistance than aluminium, giving a higher Q-factor (resulting in higher receiver gain). The fifth or sixth level of copper is also thicker (lower resistance), and further away from the substrate (less parasitic capacitances).

Figure 17:
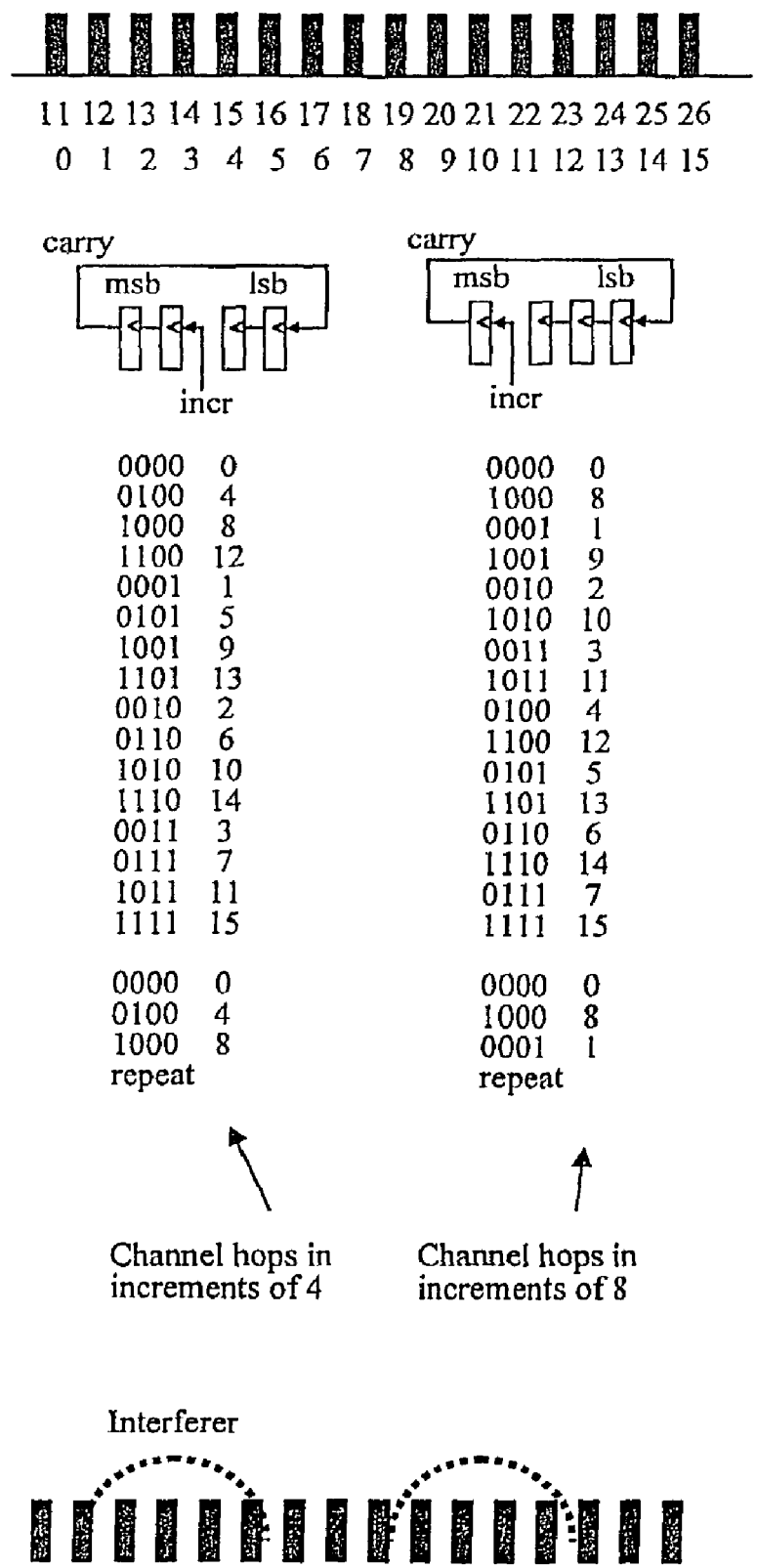
FIG. 17 is a diagram illustrating frequency selection of a wireless transceiver.

Referring to FIG. 17, frequency selection for the IEEE802.15.4 RF transceiver 3 is shown. This uses DSSS modulation, and the diagram shows the 16 DSSS channels in the 2.4 GHz ISB band as per the 802.15.4 specification. The device 1 forms a node in a wireless network of nodes. This could be a simple point-to-point link or a star or mesh network. A fixed frequency is used by all nodes as per the 801.15.4 specification. The wireless interface 3 additionally provides a slow frequency hopping scheme to circumvent interferers. It operates by all nodes using the same frequency initially. Upon a transmission failure indicating possible interference, the nodes move to a different frequency according to an algorithm illustrated in FIG. 17. There follows synchronisation of all nodes.

All nodes are pre-programmed with the hop sequence for the frequency-hopping scheme to work. Further, they must all be initialised to the same channel so that they can "hop together", typically after installation or battery replacement.

In more detail, upon installation (or battery replacement), the installer manually puts the node into "initialise" mode, by, for example, pressing a button. The node then switches on its receiver and "listens" for a nearby node transmission (or master beacon), on channel 0 for example. If it receives nothing after an appropriate time, for example a few seconds or minutes (because the current channel might be blocked), it steps to the next channel in the sequence, and again waits and listens. Eventually by this means it should receive a beacon or data packet from a neighbouring node; it can then re-synchronise its timer, request the hop interval timing, join the sequence, and go to sleep until the next hop and transmit period.

This initialisation method means the node has to stay "on" in full-power receive mode just once at installation; it can then revert to sleep mode for 99.9% of the time (as defined in the 802.15.4 standard) for the 1 to 3 year lifetime of the battery. Since the 802.15.4 standard allows for sleep periods of up to about 4 minutes, the node could be in full-power receive mode for this duration. In practice this is unlikely, however, since the installer will know about this period. Using a spectrum analyser (or hand-held wireless 'sniffer'), he can roughly predict when the next beacon transmission is due, and press the 'initialise' button just before this.

Figure 18:
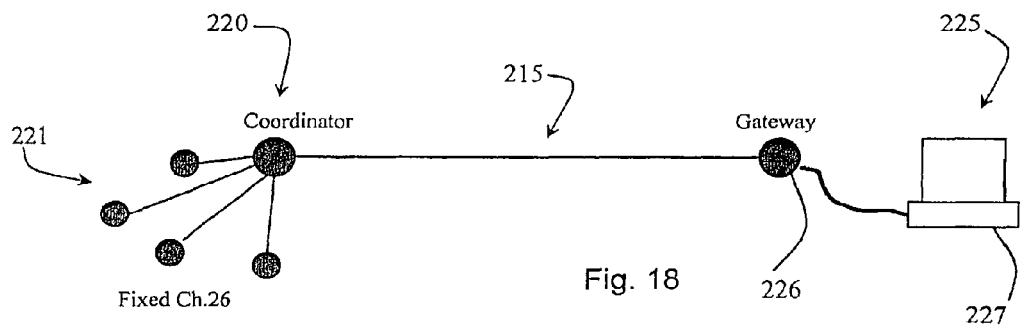
FIG. 18 shows a communication scheme for a device of the invention.

Referring to FIG. 18 this diagram shows an example of use of the slow hopping scheme. It is used on a long-distance (200 m) link 215 between two buildings 220 and 225 (using a directional 14 dBi antenna on a gateway node 226 linked with a computer 227). A standard 802.15.4 Zigbee fixed-channel star network of nodes 221 is implemented within the first building 220. This enables multi-vendor interoperable nodes to be installed in a star-network plant monitoring application, whereas the slow-hopping algorithm is employed on the long-distance critical link, which is more at risk of interference. This combination of DSSS modulation and slow Frequency Hopping provides an extremely robust and resilient solution to wireless communication.

Testing and Calibration

This is traditionally difficult for humidity sensors, requiring special chambers of controlled humidity, along with special package handling and electrical connections. In this invention, since the entire humidity sensor is fabricated in a standard CMOS process, it can be tested—and calibrated—at the normal wafer-level test before wafers are shipped. This takes advantage of the fact that wafer probe and factory test areas are generally operated at a precise humidity level, for example 40% relative humidity. This known value can be stored by the production wafer tester in on-chip Flash EEPROM memory for later use by the microcontroller in correctly calibrating the output value under software control, or it can be used in a non-Flash-EEPROM version of the chip to blow poly fuses to calibrate the sensor at 40% RH. This 1-point calibration may be sufficient for many applications, e.g. office air-conditioning control around a set-point, typically 40%. If more accuracy over a wider range of humidity is desired, then a second calibration point may be required. This is achieved by doing a "second-pass" wafer probe, in an enclosed chamber at 85% RH for example, or a dry-nitrogen desiccant chamber (0.001% RH). Although the second pass wafer test adds some additional cost, it is significantly less than package based testing—and in some cases (for example EEPROM CMOS), a second-pass wafer test is often done as standard. For this higher accuracy testing, a chilled-mirror hygrometer may be attached to monitor the humidity in the wafer tester. Chilled mirror hygrometers may be calibrated against national standard laboratories, and give humidity and dew-point readings within accuracies of 0.3% approx.

Gas Sensing

Figure 19:
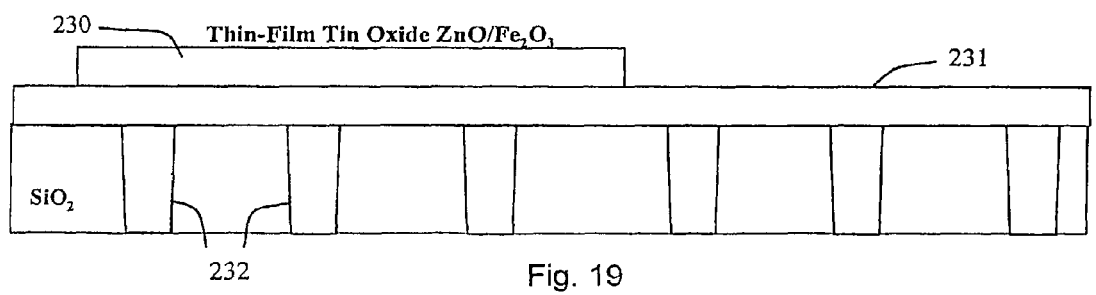
FIG. 19 is a cross-sectional diagram of a gas sensing device of the invention.

In another embodiment, illustrated in FIG. 19, a thin film 130 of zinc oxide and ferric oxide is deposited over passivation 231 at the location of one of the differential capacitors 232 of the 18-bit Sigma-Delta A-to-D converter 12. These oxides are synthesized by a sol-gel process, heated to about 120° C. to 200° C. then deposited by hybrid-ink-jet deposition. The thin-film means that small finger spacings can be used in the sensor structure, and the high-resolution A-to-D converter means that small sensor structures can be used and still result in detectable minute changes of capacitance, even at room temperature operation.

Figure 20:
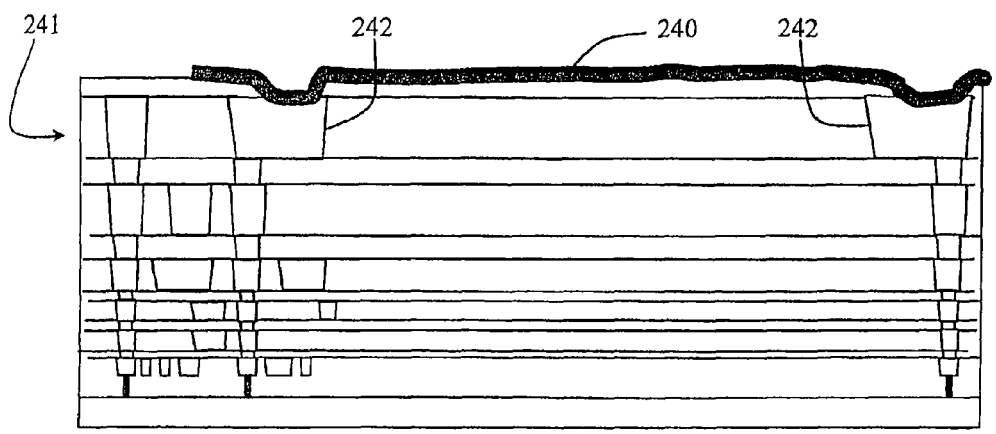
FIG. 20 is a schematic cross-sectional diagram of an audio sensor of the invention.

FIG. 20 shows an alternative embodiment, in which ferric-oxide/zinc-oxide 240 is deposited on top oxide or passivation 241, but is connected directly to electrodes 242 in the top metal layers, forming a resistor whose value can be determined as part of a bridge circuit by the 18-bit converter.

By use of different materials instead of the oxides 230 FIG. 19, the device architecture and production process may be adapted for sensing different gases, such as using palladium for hydrogen sensing, Zirconia for $SO_2$, $H_2S$, or Plasticised Polyvinyl chloride for $NO_2$, and $WO_3$ for iso-butane. In each case, both the conductivity and dielectric constant of the sensing material is changed by the ingressing gas, by absorption, or physisorption, or chemisorption. Therefore the embodiments of FIG. 19—capacitive—and FIG. 20—resistive—are used alternately or together in conjunction with the on-chip tightly integrated high resolution converter to achieve very low ppm gas concentration measurements. The presence of the microcontroller and EEPROM memory means that several new features are possible, such as look-up table calibration and scaling, offset compensation, and cross-sensor compensation, for example using humidity and temperature readings to compensate and digitally extract the correct hydrogen reading from the palladium-coated sensor structure.

Audio Sensing

A piezo-electric polymer may be applied in the configuration shown in FIG. 20 for sound sensitivity. Transduction is predominantly based on conductivity change. In this case, at the MOS circuit level a bridge circuit with buffer driving the 18-bit A-to-D converter is employed to capture the audio signal.

An audio sensor (microphone) is a useful feature on a remote wireless node, for example to "listen" if a motor is running, if an alarm bell is ringing, if an air compressor is leaking. Arrangements are needed for this audio due to the 0.1% duty cycle of IEEE802.15.4; the 250 Kb/s max data rate in the 802.15.4 2.4 GHz band corresponds to a sustained constant data rate of 250 b/s at 0.1% duty cycle. A variable-bit-rate audio compressor block (VBR) is employed to achieve 15:1 or better compression ratio, achieving an effective audio bit-rate of 3.75 Kb/s—sufficient for many industrial low-grade audio requirements.

Optical Sensing

Figure 21:
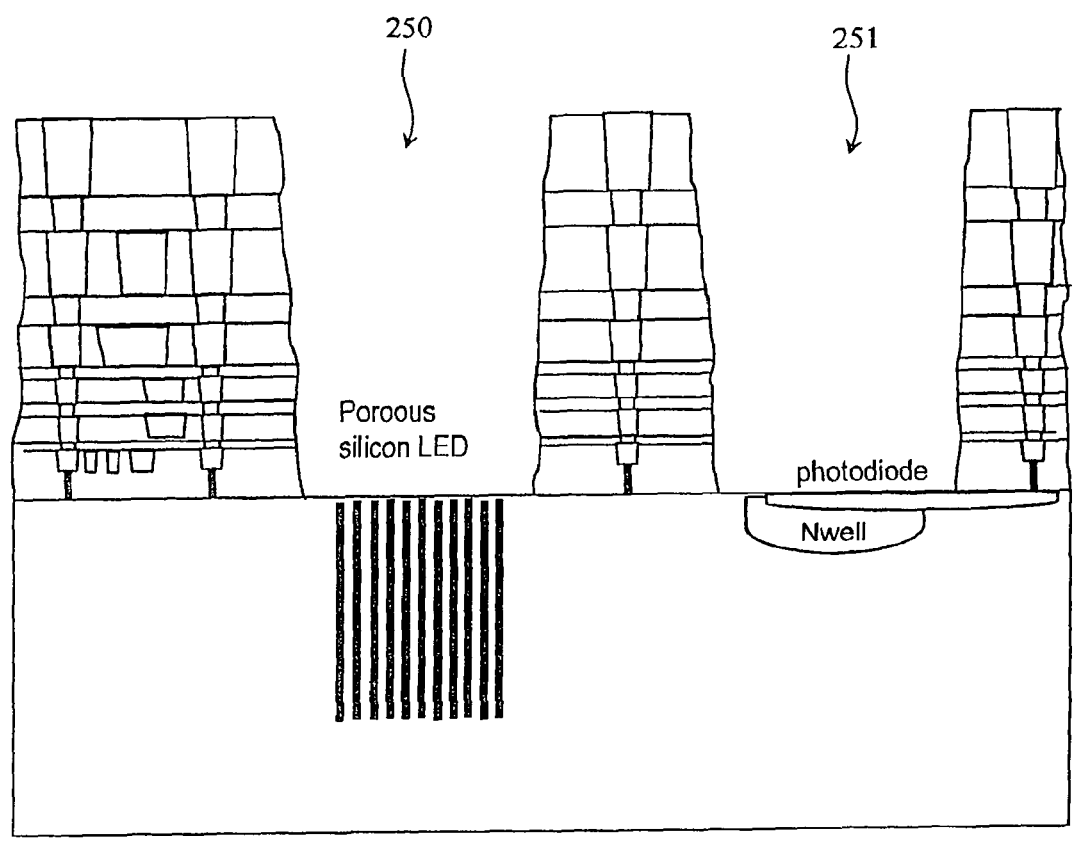
FIG. 21 is a cross-sectional view of an LED and photodiode of a device of one embodiment.

Referring to FIG. 21 the device may also include an optical emitter 150 and detector 151. Highly-directional deep anisotropic etching is employed at the end of normal processing to fully etch away all six or seven layers of dielectric to expose a photodiode light sensor 151, a large PN junction, 200 um.times.500 um, which collects photons and generates a corresponding electrical current.

The etch also reveals a porous silicon region 250 in this embodiment, created at the start of the process by electro-chemical etching of the substrate in this particular region. Passing current through this makes it function as a light emitting diode (LED) due to the well known luminescence property of porous silicon. Isolation trenches placed around the porous region can minimize any currents leaking to the substrate and improve the light efficiency.

Electrochemical etching to form porous silicon is well known to those skilled in the art, and available on some CMOS processes, but is non-standard on most CMOS processes. An alternative LED construction is a doped polymer organic light emitting device. Hybrid Ink-jet printing is used to directly deposit patterned luminescent doped-polymer films, for example polyvinylcarbazol (PVK) film, onto electrodes in the manner shown in FIG. 20.

The following are some other materials which can be added at lower temperatures, typically 300° C. or less, making them amenable to much easier integration with CMOS processes without altering any of the CMOS junction or device parameters.

One example is a Gold-Ferric-oxide combination ($AuFe_2O_3$) as a sensing layer for Carbon Monoxide. It can be sputtered onto the wafer surface at room temperature, e.g. sputter the Ferric-oxide from an $Fe_2O_3$ target or from an Iron target in an Oxygen Plasma (Reactive Sputtering), then dope or coat the Iron oxide with gold, and anneal (or sinter) at approx 250 C. This causes the gold to cluster and increases reactivity (e.g. to Carbon Monoxide) by forming $Fe_2O_3$-x at the surface, i.e. unformed bonds to which CO will attach, thereby changing the conductivity and dielectric constant of the material, which can be detected by the 18-bit A-to-D converter, as a capacitance or resistance change as per FIG. 19 or FIG. 20.

For $SO_2$ sensing, a thin-film of NNDE (N,N-diethyl-3-amino-propyl-trimethoxysilane) is applied as in FIG. 19. While this is sensitive to $SO_2$ molecules, there is a complicated interaction of temperature and humidity, for example in a humid $SO_2$ atmosphere. However the ability of the chip to also measure humidity and temperature means that the on-chip microcontroller can do a compensation calculation to extract the correct readings of $SO_2$.

Other materials which can be deposited with CMOS-compatible processing and temperatures are: Copper Bromide (CuBr) thin film for $NH_3$ detection; Polyanylene for $H_2S$ detection; $WO_3$ thin film precalcined/calcined at 280° C. for $NO_2$ detection. PVB (Poly-vinyl-Butyral): This polymer (and many other polymers) can be easily deposited on silicon wafers at room temperature, using various sol-gel, print-on, and spin-on techniques. PVB for example, when doped with Carbon-Black powder (CB), exhibits selective conductivity changes when exposed to methanol, propanol and hexanol vapours in the concentration range 1000 to 5000 ppm.

The lower temperatures and CMOS-compatibility of these materials, and the parasitic sensing method with tightly coupled high-resolution converter underneath the sensor on the same IC, all means that single-chip gas leak detectors and gas-sensors with room-temperature operating capability are enabled, with very low power, enabling battery operation. The integration on deep sub-micron CMOS, 0.18 um in this disclosure, enables the cost-effective integration of microcontroller, memory (for look-up table calibration and cross-correlation of different on-chip sensor readings) and wireless transceiver. The barrier layers on these processes prevent these gas-sensing materials from diffusing into and contaminating the other CMOS circuitry.

The invention is not limited to the embodiments described but may be varied in construction and detail. For example, conductors other than copper may be used for the interconnects, such as aluminium. Also, the sensor device may be a "stripped down" version of the sensor, a "humidity-to-digital" sensor chip, having no radio or microcontroller or flash memory. In this case, calibration of the A-to-D and sensor is achieved by blowing various poly fuses in the voltage reference circuit and capacitor array. It should be noted that testing need not involve testing every code of the A-to-D, thereby simplifying testing significantly, and reducing cost. Also, some or more of the following features may be provided individually or in combination in a method and device other than as described in the embodiments above: use of strained silicon as a low noise amplifier, low-frequency channel selection/hopping, SAR with replication of the capacitor array, and thick-oxide higher headroom; porous silicon LED, audio piezo-electric polymer microphone sensor, audio compression and transmission at low duty cycle, the microcontroller power-saving and noise reduction features.

The detecting element of a gas-sensing device may alternatively be Gold-Ferric Oxide, NNDE, Copper Bromide, Polyanylene, or WO3.

The invention claimed is:

1. An integrated gas sensor device comprising:
   a semiconductor integrated circuit formed on a single substrate, the semiconductor integrated circuit comprising:
   MOS circuits formed in the substrate;
   a plurality of interconnect levels comprised of interconnect conductors and insulating materials above the MOS circuits, the interconnect levels provided as routing interconnect levels for the semiconductor integrated circuit;
   a resistive sensor layer and a capacitive sensor layer, both the resistive sensor layer and the capacitive sensor layer being formed above the plurality of interconnect levels and being exposed to an ambient atmosphere within which a gas to be sensed may be present;
   a microcontroller coupled to the resistive sensor layer and capacitive sensor layer, the microcontroller utilizing together resistance measurements from the resistive sensor layer and capacitance measurements from the capacitive sensor layer to provide a measurement indicative of gas concentration levels; and a humidity sensor, the microcontroller utilizing humidity readings from the humidity sensor to adjust the measurement indicative of gas concentration levels.

2. The integrated gas sensor device of claim 1, the semiconductor integrated circuit further comprising a temperature sensor, the microcontroller utilizing temperature readings from the temperature sensor to adjust the measurement indicative of gas concentration levels.

3. An integrated gas sensor device comprising:
a semiconductor integrated circuit formed on a single substrate, the semiconductor integrated circuit comprising:
MOS circuits formed in the substrate;
a plurality of interconnect levels comprised of interconnect conductors and insulating materials above the MOS circuits, the interconnect levels provided as routing interconnect levels for the semiconductor integrated circuit;
a resistive sensor layer and a capacitive sensor layer, both the resistive sensor layer and the capacitive sensor layer being formed above the plurality of interconnect levels and being exposed to an ambient atmosphere within which a gas to be sensed may be present;
a microcontroller coupled to the resistive sensor layer and capacitive sensor layer, the microcontroller utilizing together resistance measurements from the resistive sensor layer and capacitance measurements from the capacitive sensor layer to provide a measurement indicative of gas concentration levels; and
a temperature sensor, the microcontroller utilizing temperature readings from the temperature sensor to adjust the measurement indicative of gas concentration levels.

4. An integrated gas sensor device comprising:
a semiconductor integrated circuit formed on a single substrate, the semiconductor integrated circuit comprising:
MOS circuits formed in the substrate;
a plurality of interconnect levels comprised of interconnect conductors and insulating materials above the MOS circuits, the interconnect levels provided as routing interconnect levels for the semiconductor integrated circuit;
a resistive sensor layer and a capacitive sensor layer, both the resistive sensor layer and the capacitive sensor layer being formed above the plurality of interconnect levels and being exposed to an ambient atmosphere within which a gas to be sensed may be present; and
a microcontroller coupled to the resistive sensor layer and capacitive sensor layer, the microcontroller utilizing together resistance measurements from the resistive sensor layer and capacitance measurements from the capacitive sensor layer to provide a measurement indicative of gas concentration levels,
wherein the capacitive sensor layer provides a variable fringe capacitance component in a capacitor structure.

5. An integrated gas sensor device comprising:
a semiconductor integrated circuit formed on a single substrate, the semiconductor integrated circuit comprising:
MOS circuits formed in the substrate;
a plurality of interconnect levels comprised of interconnect conductors and insulating materials above the MOS circuits, the interconnect levels provided as routing interconnect levels for the semiconductor integrated circuit;
a resistive sensor layer and a capacitive sensor layer, both the resistive sensor layer and the capacitive sensor layer being formed above the plurality of interconnect levels and being exposed to an ambient atmosphere within which a gas to be sensed may be present; and
a microcontroller coupled to the resistive sensor layer and capacitive sensor layer, the microcontroller utilizing together resistance measurements from the resistive sensor layer and capacitance measurements from the capacitive sensor layer to provide a measurement indicative of gas concentration levels,
wherein the resistive sensor layer forms a resistor connected to at least one of the plurality of interconnect levels.

6. The integrated gas sensor device of claim 5, the semiconductor integrated circuit further comprising an analog to digital converter coupled between the microcontroller and both of the resistive sensor layer and capacitive sensor layer.

7. The integrated gas sensor device of claim 5, the semiconductor integrated circuit further comprising a memory element coupled to the microcontroller.

8. An integrated gas sensor device comprising:
a semiconductor integrated circuit formed on a single substrate, the semiconductor integrated circuit comprising:
MOS circuits formed in the substrate;
a plurality of interconnect levels comprised of interconnect conductors and insulating materials above the MOS circuits, the interconnect levels provided as routing interconnect levels for the semiconductor integrated circuit;
a resistive sensor layer and a capacitive sensor layer, both the resistive sensor layer and the capacitive sensor layer being formed above the plurality of interconnect levels and being exposed to an ambient atmosphere within which a gas to be sensed may be present; and
a microcontroller coupled to the resistive sensor layer and capacitive sensor layer, the microcontroller utilizing together resistance measurements from the resistive sensor layer and capacitance measurements from the capacitive sensor layer to provide a measurement indicative of gas concentration levels,
wherein at least one of the resistive sensor layer and the capacitive sensor layer comprises zinc oxide and ferric oxide.

9. A method of sensing a gas concentration, comprising:
providing a semiconductor integrated circuit formed on a single substrate, semiconductor integrated circuit comprising MOS circuits;
providing a plurality of interconnect levels comprised of interconnect conductors and insulating materials above the MOS circuits, the interconnect levels provided as routing interconnect levels for the semiconductor integrated circuit;
providing a resistive sensor layer and a capacitive sensor layer, as part of semiconductor integrated circuit, above the plurality of interconnect levels and being exposed to an ambient atmosphere within which a gas to be sensed may be present;
providing a microcontroller as part of the semiconductor integrated circuit and coupled to the resistive sensor layer and capacitive sensor layer;
configuring the semiconductor integrated circuit such that resistance measurements from the resistive sensor layer and capacitance measurements from the capacitive sensor layer may be utilized together by the microcontroller to provide a measurement indicative of gas concentration levels in the ambient atmosphere; and adjusting the measurement indicative of gas concentration levels based upon humidity readings.

10. The method of claim 9, further comprising adjusting the measurement indicative of gas concentration levels based upon temperature readings.

11. A method of sensing a gas concentration, comprising:
providing a semiconductor integrated circuit formed on a single substrate, semiconductor integrated circuit comprising MOS circuits;
providing a plurality of interconnect levels comprised of interconnect conductors and insulating materials above the MOS circuits, the interconnect levels provided as routing interconnect levels for the semiconductor integrated circuit;
providing a resistive sensor layer and a capacitive sensor layer, as part of semiconductor integrated circuit, above the plurality of interconnect levels and being exposed to an ambient atmosphere within which a gas to be sensed may be present;
providing a microcontroller as part of the semiconductor integrated circuit and coupled to the resistive sensor layer and capacitive sensor layer;
configuring the semiconductor integrated circuit such that resistance measurements from the resistive sensor layer and capacitance measurements from the capacitive sensor layer may be utilized together by the microcontroller to provide a measurement indicative of gas concentration levels in the ambient atmosphere; and
adjusting the measurement indicative of gas concentration levels based upon temperature readings.

12. A method of sensing a gas concentration, comprising:
providing a semiconductor integrated circuit formed on a single substrate, semiconductor integrated circuit comprising MOS circuits;
providing a plurality of interconnect levels comprised of interconnect conductors and insulating materials above the MOS circuits, the interconnect levels provided as routing interconnect levels for the semiconductor integrated circuit;
providing a resistive sensor layer and a capacitive sensor layer, as part of semiconductor integrated circuit, above the plurality of interconnect levels and being exposed to an ambient atmosphere within which a gas to be sensed may be present;
providing a microcontroller as part of the semiconductor integrated circuit and coupled to the resistive sensor layer and capacitive sensor layer; and
configuring the semiconductor integrated circuit such that resistance measurements from the resistive sensor layer and capacitance measurements from the capacitive sensor layer may be utilized together by the microcontroller to provide a measurement indicative of gas concentration levels in the ambient atmosphere;
wherein the capacitive sensor layer provides a variable fringe capacitance for a capacitor sensor.

13. A method of sensing a gas concentration, comprising:
providing a semiconductor integrated circuit formed on a single substrate, semiconductor integrated circuit comprising MOS circuits;
providing a plurality of interconnect levels comprised of interconnect conductors and insulating materials above the MOS circuits, the interconnect levels provided as routing interconnect levels for the semiconductor integrated circuit;
providing a resistive sensor layer and a capacitive sensor layer, as part of semiconductor integrated circuit, above the plurality of interconnect levels and being exposed to an ambient atmosphere within which a gas to be sensed may be present;
providing a microcontroller as part of the semiconductor integrated circuit and coupled to the resistive sensor layer and capacitive sensor layer; and
configuring the semiconductor integrated circuit such that resistance measurements from the resistive sensor layer and capacitance measurements from the capacitive sensor layer may be utilized together by the microcontroller to provide a measurement indicative of gas concentration levels in the ambient atmosphere,
wherein the resistive sensor layer provides a variable resistance for a resistor sensor.

14. The method of claim 13, further comprising calibrating the measurement indicative of gas concentration levels in the ambient atmosphere.

* * * * *